(12) United States Patent
Gono et al.

(10) Patent No.: US 9,017,248 B2
(45) Date of Patent: Apr. 28, 2015

(54) CAPSULE BLOOD DETECTION SYSTEM AND METHOD

(75) Inventors: Kazuhiro Gono, Sagamihara (JP); Takeshi Suga, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1532 days.

(21) Appl. No.: 11/937,185

(22) Filed: Nov. 8, 2007

(65) Prior Publication Data

US 2009/0124853 A1 May 14, 2009

(51) Int. Cl.
| A61B 1/06 | (2006.01) |
| A61B 1/04 | (2006.01) |
| A61B 1/00 | (2006.01) |
| A61B 5/06 | (2006.01) |
| A61B 5/07 | (2006.01) |

(52) U.S. Cl.
CPC ............. *A61B 1/041* (2013.01); *A61B 1/00057* (2013.01); *A61B 1/00147* (2013.01); *A61B 1/042* (2013.01); *A61B 5/06* (2013.01); *A61B 5/073* (2013.01); *A61B 2560/0223* (2013.01)

(58) Field of Classification Search
CPC ............... A61B 1/041; A61B 1/00016; A61B 1/00029; A61B 1/00156; A61B 5/06; A61B 5/0075; A61B 5/145
USPC ......... 600/109, 160, 178, 322–325, 118, 310, 600/328
See application file for complete search history.

(56) References Cited

U.S. PATENT DOCUMENTS

| 4,648,892 A | 3/1987 | Kittrell et al. |
| 4,998,973 A | 3/1991 | Kikuchi |
| 5,329,922 A | 7/1994 | Atlee, III |
| 5,353,783 A | 10/1994 | Nakao et al. |
| 5,365,925 A | 11/1994 | Lee |
| 5,604,531 A | 2/1997 | Iddan et al. |
| 5,833,603 A | 11/1998 | Kovacs et al. |
| 6,030,365 A | 2/2000 | Laufer |
| 6,104,941 A | 8/2000 | Huey et al. |

(Continued)

FOREIGN PATENT DOCUMENTS

| CN | 1509152 | 6/2004 |
| CN | 1678239 | 10/2005 |

(Continued)

OTHER PUBLICATIONS

The Chinese Office Action including its English translation, issued on May 25, 2011, in related Chinese patent application No. 200880115162.2.

(Continued)

*Primary Examiner* — Anhtuan T Nguyen
*Assistant Examiner* — William Chou

(57) ABSTRACT

A capsule for determining the blood content of living tissue in vivo in a patient to detect tumors. The capsule includes a light source and a light detector for directing light onto the tissue and for receiving interacted light therefrom. By analyzing the interacted light, a determination can be made of the blood content of that tissue. There are various ways of positioning the capsule so that it contacts the tissue in the desired orientation of the light source and light detector. There is also a system for determining the actual contact between the capsule and the tissue. A calibration system is also used that allows a self calibration that can be carried out easily and accurately just prior to the use of the capsule.

16 Claims, 10 Drawing Sheets

(56) References Cited

U.S. PATENT DOCUMENTS

| | | |
|---|---|---|
| 6,226,540 B1 | 5/2001 | Bernreuter |
| 6,393,311 B1 | 5/2002 | Edgar, Jr. et al. |
| 6,516,209 B2 | 2/2003 | Cheng et al. |
| 6,639,674 B2 | 10/2003 | Sokolov et al. |
| 6,640,117 B2 | 10/2003 | Makarewicz et al. |
| 6,692,494 B1 | 2/2004 | Cooper et al. |
| 6,738,654 B2 | 5/2004 | Sohrab |
| 6,876,448 B2 | 4/2005 | Imura et al. |
| 6,951,536 B2 | 10/2005 | Yokoi et al. |
| 7,118,529 B2 | 10/2006 | Glukhovsky et al. |
| 7,468,044 B2 | 12/2008 | Iddan |
| 7,492,935 B2 | 2/2009 | Glukhovsky |
| 7,561,908 B2 | 7/2009 | Glukhovsky et al. |
| 7,618,376 B2 | 11/2009 | Kimball |
| 7,637,864 B2 | 12/2009 | Yokoi et al. |
| 7,704,205 B2 | 4/2010 | Mizuno |
| 7,724,928 B2 | 5/2010 | Glukhovsky et al. |
| 7,792,344 B2 | 9/2010 | Wang et al. |
| 7,914,442 B1 | 3/2011 | Gazdzinski |
| 2002/0026098 A1 | 2/2002 | Kobayashi |
| 2002/0042562 A1 | 4/2002 | Meron et al. |
| 2002/0111544 A1 | 8/2002 | Iddan |
| 2002/0115908 A1 | 8/2002 | Farkas et al. |
| 2002/0177779 A1 | 11/2002 | Adler et al. |
| 2003/0085994 A1 | 5/2003 | Fujita et al. |
| 2004/0171915 A1* | 9/2004 | Glukhovsky et al. ......... 600/160 |
| 2004/0215068 A1 | 10/2004 | Lykke et al. |
| 2004/0249254 A1 | 12/2004 | Racchini et al. |
| 2004/0249291 A1 | 12/2004 | Honda et al. |
| 2005/0033276 A1 | 2/2005 | Adachi |
| 2005/0075551 A1 | 4/2005 | Horn et al. |
| 2005/0085696 A1 | 4/2005 | Uchiyama et al. |
| 2005/0148847 A1 | 7/2005 | Uchiyama et al. |
| 2005/0154277 A1* | 7/2005 | Tang et al. ..................... 600/407 |
| 2005/0267340 A1 | 12/2005 | Ishihara |
| 2006/0178557 A1 | 8/2006 | Mintchev et al. |
| 2007/0088220 A1 | 4/2007 | Stahmann |
| 2007/0106147 A1 | 5/2007 | Altmann et al. |
| 2007/0129615 A1 | 6/2007 | Backman et al. |
| 2007/0179368 A1 | 8/2007 | Backman et al. |
| 2007/0244402 A1 | 10/2007 | Brockway et al. |
| 2007/0299309 A1* | 12/2007 | Seibel et al. .................. 600/117 |
| 2008/0125623 A1 | 5/2008 | Tamura et al. |
| 2008/0200784 A1 | 8/2008 | Cheng |
| 2009/0093728 A1* | 4/2009 | Hyde et al. .................... 600/476 |
| 2009/0312618 A1 | 12/2009 | Hengerer et al. |

FOREIGN PATENT DOCUMENTS

| | | |
|---|---|---|
| EP | 1 695 662 A | 8/2006 |
| JP | H04-144533 | 5/1992 |
| JP | 5-115463 | 5/1993 |
| JP | H05-200015 | 8/1993 |
| JP | H10-243920 | 9/1998 |
| JP | 2001-204685 | 7/2001 |
| JP | 2003-210394 | 7/2003 |
| JP | 2005-073887 | 3/2005 |
| JP | 2005-124708 | 5/2005 |
| JP | 2005-192879 | 7/2005 |
| JP | 2005-328990 | 12/2005 |
| JP | 2006-304995 | 11/2006 |
| JP | 2007-51879 | 3/2007 |
| KR | 10-2003-0071820 | 9/2003 |
| KR | 10-2005-0095639 | 9/2005 |
| KR | 10-2007-0047221 | 5/2007 |
| WO | 02055984 | 7/2002 |
| WO | 02073507 | 9/2002 |
| WO | 2004032621 | 4/2004 |
| WO | 2005031650 | 4/2005 |
| WO | 2005039402 | 5/2005 |
| WO | 2005113021 | 12/2005 |
| WO | 2007113165 | 10/2007 |

OTHER PUBLICATIONS

The Written Opinion, mailed on Apr. 24, 2009, in related PCT application No. PCT/JP2008/070825.

The Int'l Search Report and Written Opinion, mailed on Mar. 3, 2009, in related PCT application No. PCT/JP2008/070962.

The Int'l Search Report and Written Opinion, mailed on Mar. 5, 2009, in related PCT application No. PCT/JP2008/070827.

The Office Actions mailed on Dec. 28, 2010, Jun. 2, 2011, Oct. 18, 2011 and Nov. 29, 2011, in related U.S. Appl. No. 11/937,153.

The Office Actions mailed on Apr. 28, 2011 and Nov. 14, 2011, in related U.S. Appl. No. 11/937,133.

FEHER; 931111, Thermoelectric Air Condo Variable Temperature Seat (VTS) . . . ; Copyright 1998 Society of Automotive Engineers, Inc. pp. 341-349.

FEHER; 980661, Stirling Air Cond. Variable Temperature Seat, (SVTS) . . . ; Copyright 1998 Society of Automotive Engineers, Inc. pp. 1-9.

International Search Report for related application PCT/US06/34587, dated Oct. 5, 2007.

Office Actions from related U.S. Appl. No. 11/243,604, dated Feb. 6, 2007 and Jul. 9, 2007.

Office Actions from related U.S. Appl. No. 11/097,941; dated May 4, 2007 and Sep. 4, 2007.

Office Actions from related abandoned U.S. Appl. No. 08/298,457; dated Sep. 27, 1995 and Mar. 27, 1996.

Office Actions from related U.S. Appl. No. 09/126,914 (US 6,263,530); dated Oct. 12, 1999.

Office Actions from related U.S. Appl. No. 08/710,959 (US 6,085,369); dated Apr. 17, 1997; Oct. 16, 1997; Mar. 30, 1998; and Dec. 23, 1998.

EP301606 Office Action, dated Sep. 24, 2003 from related U.S. Appl. No. 08/710,959 (US 6,085,369).

The International Search Report and Written Opinion mailed on Sep. 15, 2009 in related PCT Application No. PCT/JP2009/060570.

The International Search Report and Written Opinion mailed on Jul. 21, 2009 in related PCT Application No. PCT/JP2009/061790.

Japanese Office Action mailed on Feb. 28, 2012 in related Japanese Patent Application No. 2010547769.

Japanese Office Action mailed on Oct. 30, 2012 in related Japanese Patent Application No. 2010-517222.

Japanese Office Action mailed on Oct. 30, 2012 in related Japanese Patent Application No. 2010-517225.

Office Action mailed on Aug. 30, 2012, in related U.S. Appl. No. 11/937,153.

Office Action mailed on Mar. 5, 2012 in related U.S. Appl. No. 11/937,133, now U.S. Patent No. 8,162,828.

Office Actions mailed on Nov. 29, 2010, May 26, 2011, Oct. 28, 2011, Nov. 25, 2011 and Aug. 20, 2012, in related U.S. Appl. No. 12/132,932.

Office Actions mailed on Mar. 26, 2010, Sep. 14, 2010, Dec. 9, 2010, May 9, 2011 and Oct. 24, 2011, in related U.S. Appl. No. 12/171,505, now U.S. Patent No. 8,093,548.

Katzir, "Biometrical Fiberoptic Sensors," 1988, Optical Society of America, 1988 Technical Digest Series, vol. 2, pp. 4-6.

Chinese Office Action, issued on Nov. 20, 2013, in the corresponding Chinese application No. 200880115052.6, and English translation thereof.

The Decision of a Patent Grant, issued on Aug. 5, 2014, in the corresponding Japanese application No. 2013-169956, and an English language translation thereof.

* cited by examiner

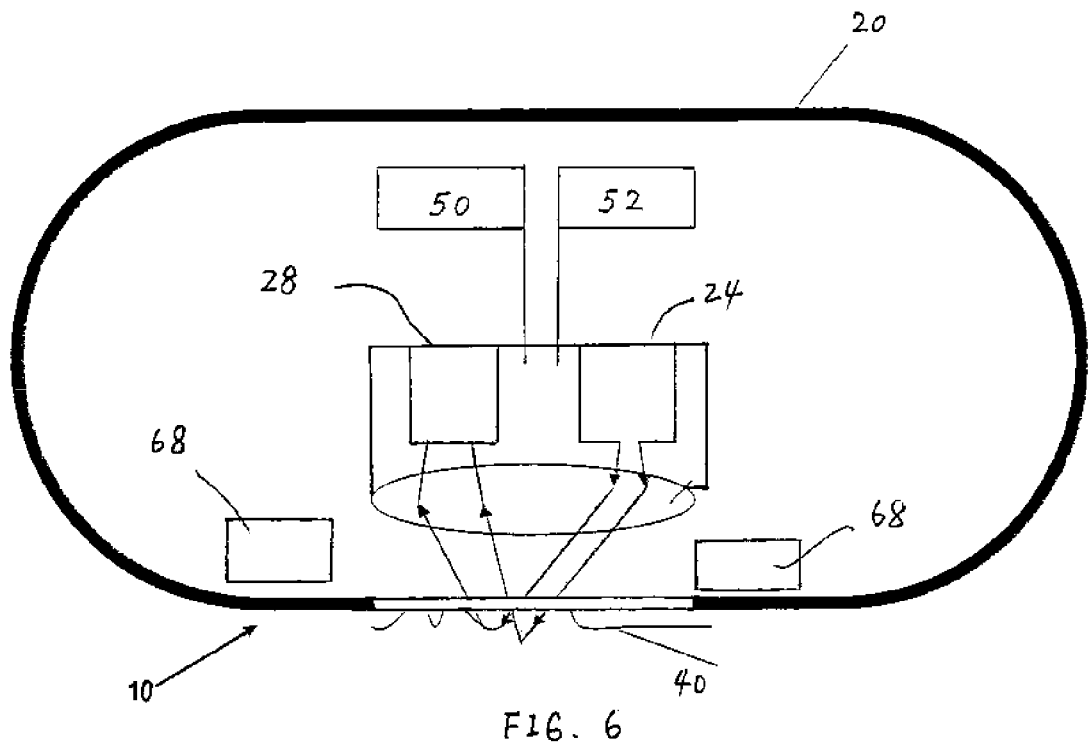
FIG. 6
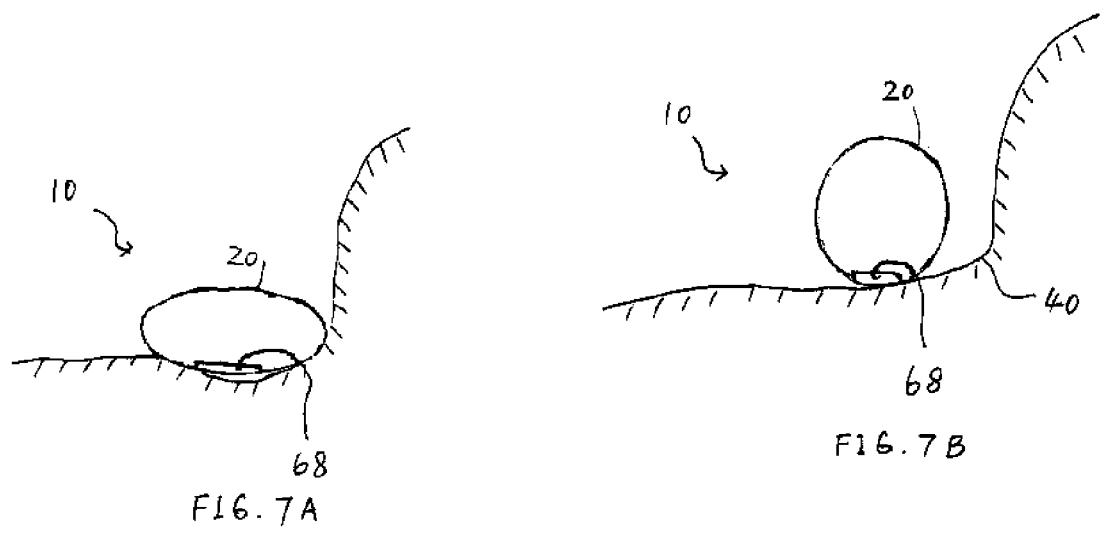
FIG. 7A
FIG. 7B

CAPSULE BLOOD DETECTION SYSTEM AND METHOD

CROSS REFERENCE TO RELATED APPLICATIONS

This application is related to U.S. patent application Ser. No. 11/937,153 filed concurrently herewith, entitled "Method and Solution for Correlating Image and Tissue Characteristic Data" and U.S. patent application Ser. No. 11/937,133, filed concurrently herewith, entitled "Blood Content Detecting Capsule," now U.S. Pat. No. 8,162,828 issued Apr. 24, 2012, both of which are herein incorporated by reference.

FIELD OF THE INVENTION

The invention relates to the use of capsule type endoscopes in patients. More specifically, the invention relates to detecting, positioning, and calibrating capsule type endoscopes for use in a living patient with the goal of utilizing blood content detection to locate and determine abnormalities in living tissue.

BACKGROUND OF THE INVENTION

Endoscopes have long been used by physicians to enter into the internal area of a patient in order to carry out function at that location. Traditionally, the endoscope comprises an optical system and an illumination system that enable the physician to locate the distal end of the endoscope in the desired area to enable the physician to view that area at a location external of the patient.

More recently, there has been developed capsule endoscopes which are capsules containing image capture devices, such as digital cameras, that are swallowed by the patient and travel to a location of interest within the patient, such as the intestinal track, to study the colon in a search for lesions. Once at that location, the capsule endoscope gathers captured images to aid the physician to carry out some diagnosis of the patient.

Moreover, scientists have discovered a detectible increase in the blood content of superficial mucous membrane proximate cancerous and precancerous lesions in the colon as described, for example, in R. K. Wali, H. K. Roy, Y. L. Kim, Y. Liu, J. L. Koetsier, D. P. Kunte, M. J. Goldberg, V. Turzhitsky, and V. Backman, *Increased Microvascular Blood Content is an Early Event in Colon Carcinogenesis*, Gut Vol. 54, 654-660 (2005), which is incorporated by reference herein. This phenomenon is referred to as an early increase in blood supply (EIBS).

BRIEF SUMMARY OF THE INVENTION

The invention relates to swallowable capsules having the capability to measure blood content of tissue comprising, for example, the digestive track. Exemplary configurations of such devices are described in related corresponding patent applications entitled "Method and Solution for Correlating Image and Tissue Characteristic Data" and "Blood Content Detecting Capsule" co-filed herewith and incorporated by reference herein. Such devices enable doctors and clinicians to detect EIBS for screening of lesions or tumors or when combined with image capture devices within the capsules facilitate the location of cancerous and pre-cancerous lesions or tumors.

Exemplary configurations for such capsule include, for example, a light source that emits polarized light onto a region of the superficial mucous membrane and a light detector that receives light interacted with that tissue and the hemoglobin contained therein. The interacted light from the tissue is returned at a different polarization angle than the emitted light. This return angle and magnitude of the detected interacted light can be measured and is indicative of the blood content in that mucus tissue. Thus, the information relative to the blood content can be transmitted by the capsule to a receiving instrument external of the patient so that the physician can monitor the blood content in the tissue and use that information in determining the existence or proximate location of a lesion. A technique for the measurement of Hb through the use of polarized light has been disclosed in Y. L. Kim, Y. Liu, R. K. Wali, H. K. Roy, M. J. Goldberg, A. K. Kromin, K. Chen, and V. Backman, *Simultaneous measurement of angular and spectral properties of light scattering for characterization of tissue microarchitecture and its alteration in early precancer*, IEEE J. Sel. Top. Quant. Elec., Vol. 9, 243-256 (2003) and M. P. Siegel, Y. L. Kim, H. K. Roy, R. K. Wali, and V. Backman, *Assessment of blood supply in superficial tissue by polarization-gated elastic light-scattering spectroscopy*, Applied Optics, Vol. 45, 335-342 (2006) and the entirety of those articles are incorporated herein by reference.

However, one issue confronted by such a capsule is that it is necessary for the capsule to be in direct contact with the tissue, or at least in extremely close proximity thereto for the light source and light detector to accurately detect blood content. As such, because the capsule itself is not readily maneuverable within the patient, there must be system that enables the capsule to be positioned in the proper orientation with respect to the tissue. Another issue with the use of such a capsule is that it is further important that there be some system that verifies the existence of the contact so that the capsule can actually obtain valid information as to the blood content in that tissue. Also, it is important that there be some calibration system for the blood content detection system of the capsule that is extremely reliable and that can be used on site prior to use with a patient.

The present invention provides methods and capsule devices that overcome these issues. In accordance with the present invention, a capsule is provided that is small enough to be swallowed by a patient and it has a blood content detector contained therein. The blood content detector includes a light source and a light detector oriented such that polarized white light from the light source travels through a measurement widow formed in the capsule to impinge upon living tissue of the patient where interacted light from the tissue and hemoglobin contained therein is detected by the light detector. The angle of the reflected light is analyzed as indicative of blood content in that tissue and generates signals representative of that blood content that are transmitted to a data processing means, such as a computer, where the information as to the blood content is processed and made available to a user.

As such, the present invention includes various means to orient the capsule so that it is in actual contact with the tissue being analyzed and the light impinges upon the tissue. To that end, one embodiment uses the shape of the capsule to achieve the desired orientation. Another embodiment provides weights strategically located within the capsule to bring about the desired orientation and yet another embodiment has the blood content detector mounted within a inner module that is movable within an outer capsule. In one exemplary embodiment, mirrors are provided to direct the light from the illuminating means to the light receiving means in order to further miniaturize the capsule.

The present invention also includes a proximity detector that detects the proximity of the capsule detector to the living tissue and, in particular, to verify when there is an actual contact between the capsule and that tissue. The proximity detector can be of various types and may include a distance detection system that determine the distance between the capsule and the living tissue so that a signal can be provided as that actual contact is imminent so that a blood content measurement can be taken at the time of contact.

Finally, there is a calibration system that can be used to calibrate the capsule easily and accurately just prior to the time of use.

These and other features and advantages of the present invention will become more readily apparent during the following detailed description taken in conjunction with the drawings herein.

BRIEF DESCRIPTION OF THE DRAWINGS

FIG. 2 is a schematic view of an exemplary embodiment of the capsule;

FIG. 6 is a cross sectional diagram showing another exemplary embodiment of the present invention;

FIGS. 7A-7B are cross sectional diagrams illustrating the exemplary use of weights to position a blood content detector of the present invention;

DETAILED DESCRIPTION OF THE INVENTION

Figure 1:
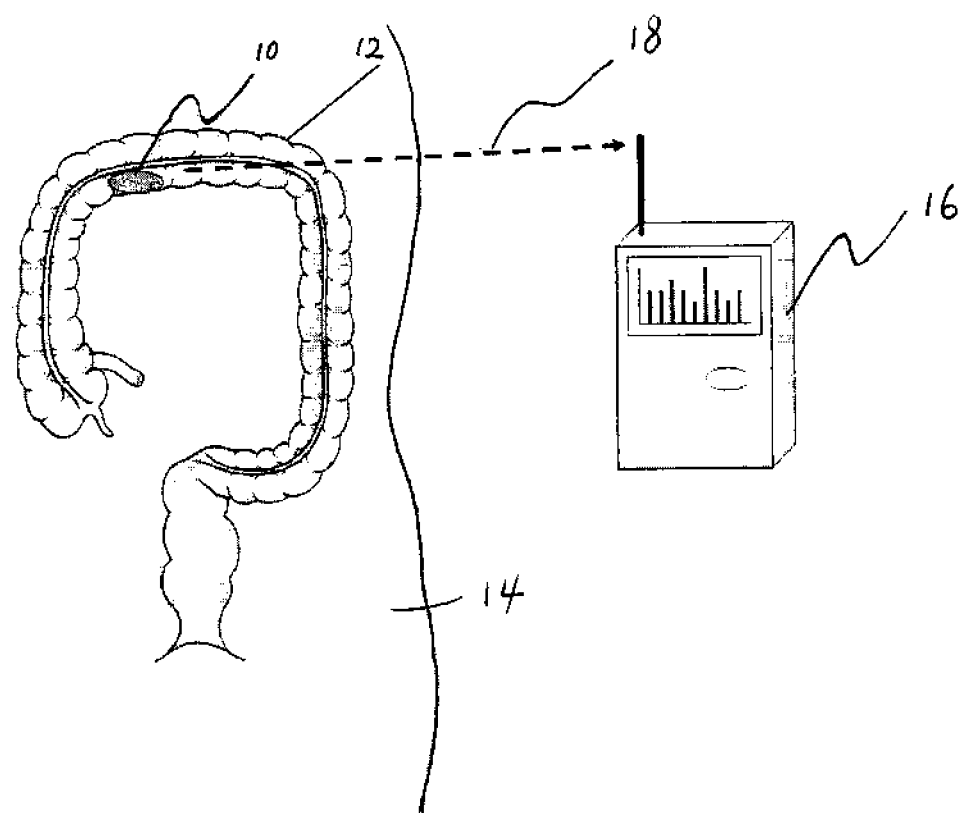
FIG. 1 is a schematic view of an exemplary in vivo sensing system in accordance with the present invention.

Referring first to FIG. 1, there is shown a schematic view of an in vivo sensing system illustrating the use of the present invention. In FIG. 1, therefore, there can be seen a capsule 10 that is moving slowly in the colon 12 of a patient 14 and an external processing unit 16 that receives data sent from the capsule 10, analyzes that data and displays the result. The stream of data and information can be, for example, communicated wirelessly along the path 18 to the external processing unit 16.

In an exemplary configuration of the capsule 10, two pieces of spectrum information of body living tissue are acquired to obtain information about the blood content in the superficial portion of the mucous membrane or other living tissue. This embodiment uses a polarization spectrum of a first orientation having the same polarization direction as incident light from a capsule light source, referred to as a horizontal polarization and a corresponding orthogonal polarization spectrum which has the polarization direction perpendicular to incident light from the capsule light source. As stated, a technique for determining the hemoglobin content of tissue through the use of polarized light has been disclosed in Y. L. Kim, Y. Liu, R. K. Wali, H. K. Roy, M. J. Goldberg, A. K. Kromin, K. Chen, and V. Backman, *Simultaneous measurement of angular and spectral properties of light scattering for characterization of tissue microarchitecture and its alteration in early precancer*, IEEE J. Sel. Top. Quant. Elec., Vol. 9, 243-256 (2003) and M. P. Siegel, Y. L. Kim. H. K. Roy, R. K. Wali, and V. Backman, *Assessment of blood supply in superficial tissue by polarization-gated elastic light-scattering spectroscopy*, Applied Optics, Vol. 45, 335-342 (2006) and the entirety of those articles are incorporated herein by reference.

In this embodiment, a difference operation between the first or horizontal polarization spectrum and the perpendicular polarization spectrum is performed in the capsule 10 and the result is transmitted to the processing unit 16. It is alternatively suitable in accordance with the invention for the difference operation to be carried out in the processing unit 16 or other external device whereby data indicative of the horizontal polarization spectrum and the perpendicular spectrum are sent to the processing unit 16 by the capsule 10.

Figure 2:
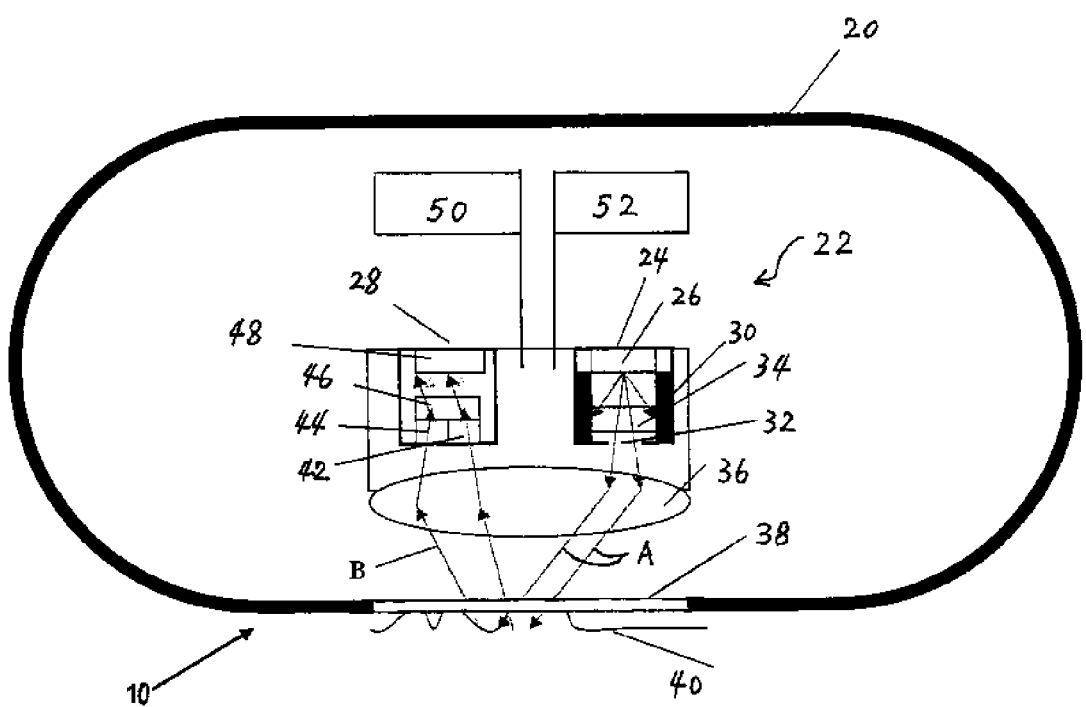
FIG. 2 is a cross sectional diagram showing an exemplary capsule constructed in accordance with the present invention.

Referring now to FIG. 2, there is shown a cross sectional diagram showing the construction of an exemplary capsule 10 of the present invention. As can be seen, the capsule 10 comprises an enclosure 20 with the components of the device encased within the enclosure 20. The enclosure 20 is designed to be of a size that is relatively easy for a patient to swallow and can generally have a diameter of approximately 10 mm.

Contained within the enclosure 20, there can be seen a blood content detector 22 which includes various components used to determine the blood content of living tissue by means of an optical detector. There is, therefore a light detector 28 and a light source 24 including, for example a white LED 26. The path of the light travels in the direction of the arrows A, where the wide angle light is absorbed by light absorbing member 30 so that only a narrow angle of light (close to parallel light) can pass through an opening 32 after passing through a linear polarizing element 34 where the light is polarized. By reducing the size of the opening 32, the illuminated region of tissue can likewise be reduced. A suitable size of an illumination region can be, for example, in the range of approximately 0.1 $mm^2$ and 100 $mm^2$.

The polarized light thereafter passes through a lens 36 and opening 32 and the linear polarizing element 34 are disposed along the location of the focal length of the lens. As such, the light coming for the light source 24 and is a narrow-angle light that impinges on a small region of tissue. Furthermore, it is possible to alter the direction in which the parallel light travels by using lens to direct through a measurement window 38 to impinge upon living tissue 40 of the patient in vivo.

Interacted light from living tissue 40 and the hemoglobin contained therein returns along the direction of the arrows B to the light detector 28 as light with a specific reflection angle. As can be seen, the return interacted light passes again through the optical light path converter 36 where the light thereafter passes through two linear polarizing elements, that is, a first linear polarizing element 42 and a second linear polarizing element 44 that are orthogonal to each other. By that means, the linear polarizing elements 42 and 44 transmit beams of polarized light perpendicular to each other and the polarization direction of the first linear polarizing element 42 of the light receiving means 28 is the same as that of the linear polarizing element 34 of the illuminating means 24, and the second linear polarizing element 44 passes through the polarization spectrum orthogonal thereto. Beams of light that have been transmitted through each of the linear polarizing elements 42, 44 are passed on by a transmissive grating 46 in the directions with the different diffusion angles for each wavelength of light. That light then is sensed by a light sensor 48.

By doing so, each wavelength component of light can reach different locations on a light sensor 48 which enables spectroscopy in two kinds of polarization states; the horizontal polarization spectrum and the perpendicular polarization spectrum. Measured spectrum data is then sent to a data transmitter 50 where it is transmitted to the processing unit 16 of FIG. 1. A power supply 52 powers the components of the capsule 10.

Figure 3:
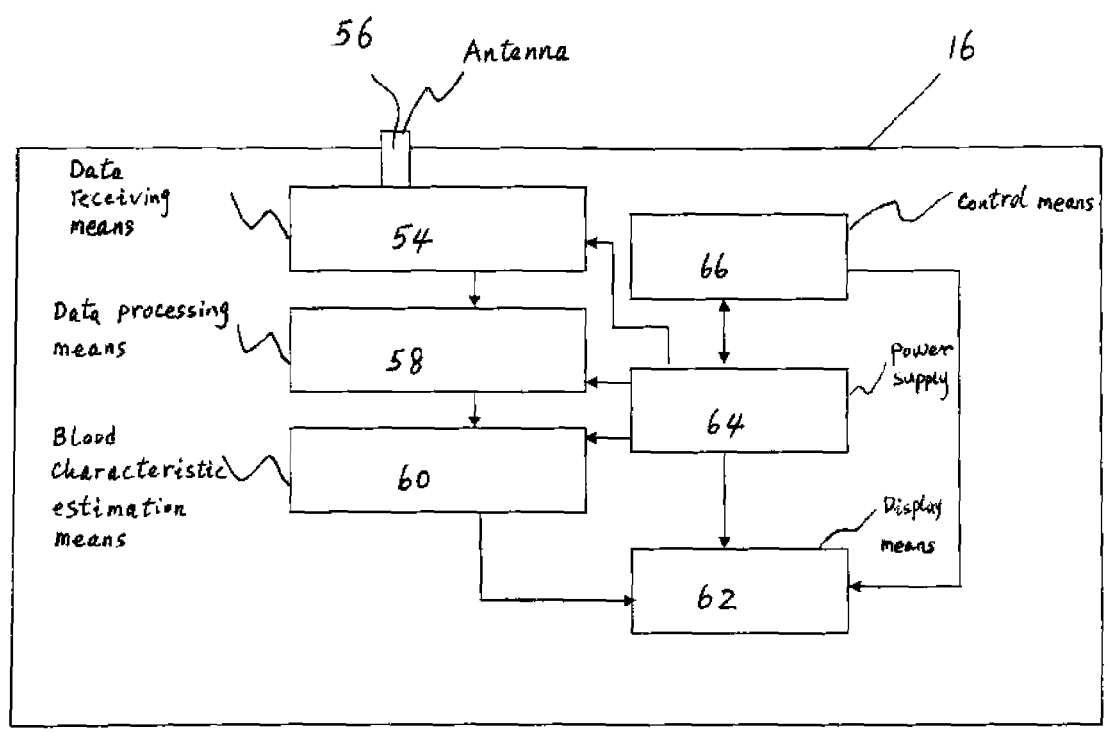
FIG. 3 is block diagram illustrating the functions carried out within an exemplary processing apparatus of the present invention.

Turning now to FIG. 3, there is shown a block diagram illustrating the functions carried out within the processing unit 16. Initially there is a data receiving means 54 that receives the information and data from the capsule 10 (FIG. 1) via an antenna 56. In the embodiment, although wireless radio transmission is expected, data transmission using alternative techniques such as acoustic or infrared schemes are likewise useable in accordance with the invention. In such case, a data transmitter in the capsule and a data receiver in the processing unit would be provided that conform to another's technology, accordingly.

The data received by the data receiver 54 is provided to a data preprocessor 58. The data preprocessor 58 executes white correction. Equation (1) shows an example of white correction.

$$\Delta Ic(\lambda) = \Delta I(\lambda)/\Delta Iw(\lambda) = (I_{II}(\lambda) - I\perp(\lambda))/(Iw_{II}(\lambda) + Iw\perp(\lambda)) \quad (1)$$

In equation (1), $\lambda$ represents wavelength. $\Delta I(\lambda)$ indicates the measured difference polarization spectrum. $\Delta Iw(\lambda)$ is a spectrum measured by using what is known as a standard white plate and is calculated by summing the white horizontal polarization spectrum $Iw_{II}(\lambda)$ and the white perpendicular polarization spectrum $Iw\perp(\lambda)$ as shown in the denominator of equation (1). In the numerator of equation (1), the difference between the horizontal polarization spectrum $I_{II}(\lambda)$ and the perpendicular polarization spectrum $I\perp(\lambda)$ is calculated in data transmitter 50 and a signal indicative of $\Delta I(\lambda)$ is transmitted by data transmitter 50 to the processing unit 16.

The blood content estimator 60 calculates the blood content by using equation (2) below, which is shown in, for example, M. P. Siegel, Y. L. Kim, H. K. Roy, R. K. Wali, and V. Backman, *Assessment of blood supply in superficial tissue by polarization-gated elastic light-scattering spectroscopy*, Applied Optics, Vol. 45, 335-342 (2006).

$$\Delta I(\lambda) = \Delta I_{scattering}(\lambda) \exp[-\alpha A_{PG}(\lambda)] \quad \text{equation (2)}$$

As stated, the blood content estimator 60 calculates the blood quantity by using a model equation, such as equation (2), and provides a corresponding blood content value to an indicator such as, for example, display 62. The corresponding blood characteristic information can then be displayed to the user by display 62. In addition there is a power supply 64 to power the processing unit 16 and a controller 66 to carry out the various control functions needed to process and display the information.

Figure 4:
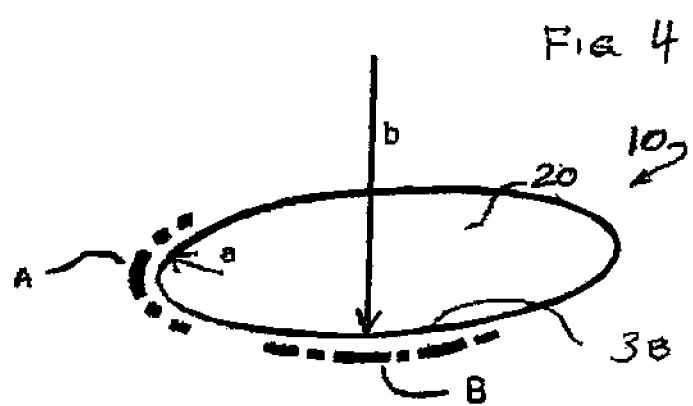
FIG. 4 is a cross sectional schematic showing an exemplary shape of a capsule in accordance with the present invention.

Turning now to FIG. 4, there is shown a schematic view of exemplary embodiment of the capsule 10 wherein cross section of enclosure 20 is a substantially elliptical shape. Because enclosure 20 has the substantially elliptical shape, the elongated regions along larger curvature B will more likely be positioned along tissue as it traverses the digestive tract than the region of smaller curvature A. Thus, measurement window 38 is located in the region along the larger curvature B.

Returning briefly to FIG. 2, it can be seen that the measurement window 38 is disposed in that downward location. The measurement window 38 is disposed in such location in FIG. 2 and the lens 36, the light source 24 and the light detector 28 are disposed on the device facing the measurement window 38 in order to direct the illumination light on a desired location of the living tissue 40.

While the capsule 10 in the prior exemplary embodiment is based upon orienting the measurement window by the characteristic shape of the capsule enclosure 20, a further exemplary embodiment achieves the proper orientation by means of the weight balance of the capsule enclosure 20.

Figure 5:
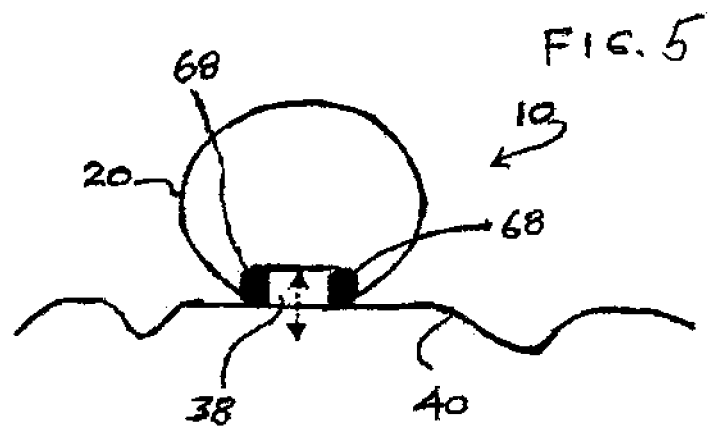
FIG. 5 is cross sectional schematic showing a further exemplary embodiment of the invention.

Accordingly, turning to FIG. 5, there is shown a capsule 10 where the enclosure 20 itself is circular in cross section and weights 68 are provided proximate the measurement window 38. The weights 68 are provided at a location away from the center of the capsule 10. When the center of gravity deviates from the center of the enclosure 20, the outer surface of the enclosure 20 in the deviated direction is likely to come into contact with the living tissue 40 of the patient as shown in FIG. 5.

As such, the measurement window 38 in this embodiment is located along the outer surface of the capsule enclosure 20 in the deviated direction, thus locating the measurement window 38 in the desired position contacting the living tissue 40 so as to attain the same effect as the embodiment of FIG. 4, the difference being that with this embodiment, the orientation of the capsule 10 is achieved by the addition of weights 68, whereas with the prior embodiment, the desired orientation was achieved by the shape of the capsule 10 itself.

Turning now to FIG. 6, there is shown a cross sectional diagram showing the exemplary embodiment of FIG. 2 using the same identification numbers as were used in FIG. 2 for corresponding features. As can be seen in FIG. 6, however, there has been added the weights 68 that are located at the sides of the measurement window 38 so as to orient the capsule 10 in contact with the living issue 40 in order to properly direct the light toward the living tissue 40 and to receive the return reflected light.

The weights 68 can be made of metal such as stainless steel or glass with a relatively high specific gravity. Even when the shape of the capsule 10 is of an elliptical shape as shown in FIG. 4, the measurement window 38 may be located in any given position by means of a weight. As can be seen in FIGS. 7A and 7B, even if the measurement window cannot be disposed or located in the desired position as shown in FIG. 7A, a measurement can be made as shown in FIG. 7B. As can be seen, the weight of the weight 68 is not specified and may vary according to the design of the capsule. It is established so that the measurement window faces downwardly when the capsule 10 is disposed on a flat panel set perpendicular to the vertical direction.

Figure 8:
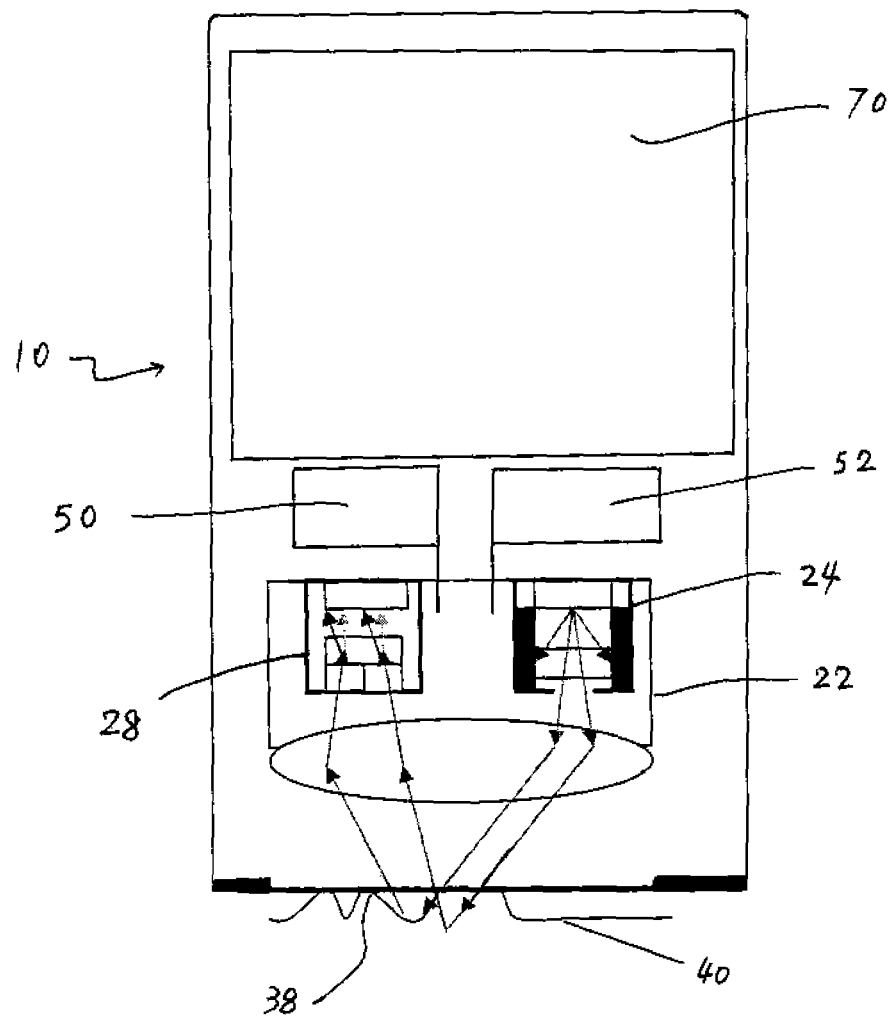
FIG. 8 is a cross sectional diagram illustrating an alternate orientation system of the present invention relative to that shown in FIGS. 7A-7B.

Turning next to FIG. 8, there is shown a cross sectional diagram showing another exemplary embodiment of the present invention. In this embodiment, instead of the use of weights, the desired orientation of capsule 10 is achieved by deviating the center of gravity from the center of the capsule 10, i.e., that is, by changing the layout within the capsule 10. In FIG. 8, the center of gravity can be made to deviate by partially placing a hollow or lightweight part 46 in the upper position so that the measurement window 38 faces downwardly to contact the living tissue 40.

Figure 9:
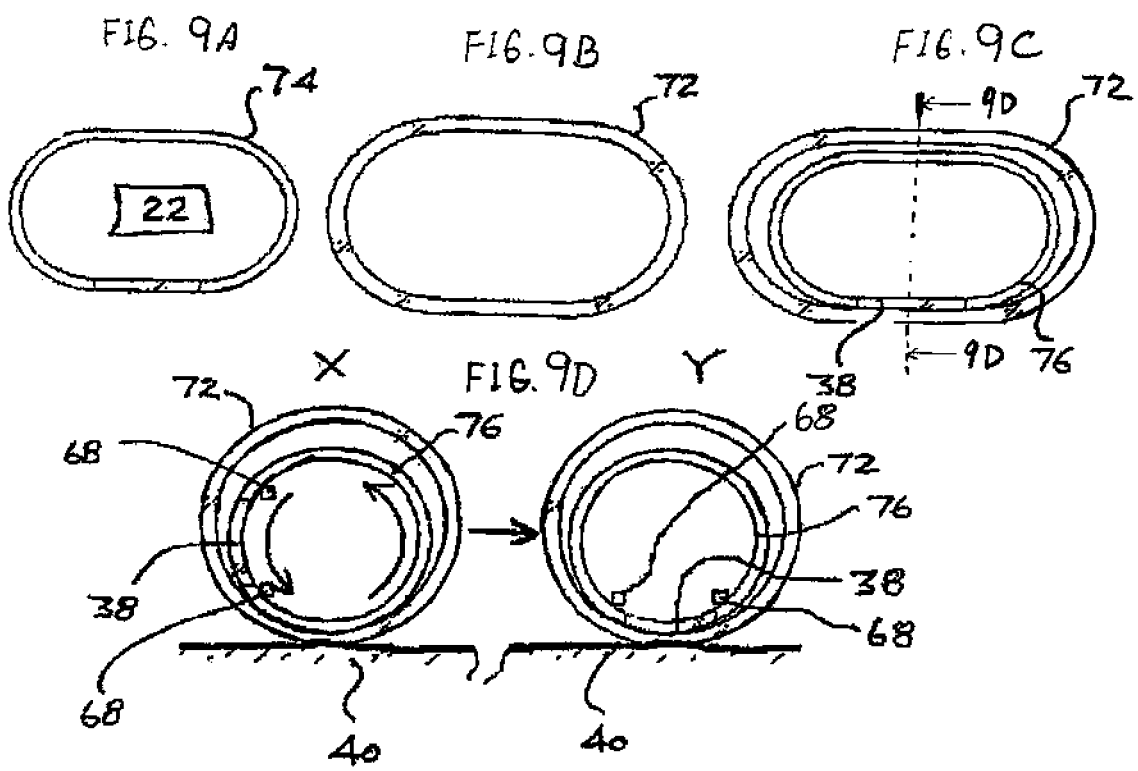
FIGS. 9A-9D are cross sectional diagrams illustrating a further orientation system of the present invention.

Turning now to FIGS. 9A-9D, there is shown a still further exemplary embodiment of the present invention. In this embodiment there is an outer capsule 72 that is comprised of a transparent material to allow the transmission of light therethrough. Within that outer capsule 72, there is disposed a moveable inner module 74 having mounted therein, the blood content detector 22. As such, in FIG. 9A, there is a cross sectional diagram of the inner module 74 and in FIG. 9B, there is a cross sectional diagram of the outer capsule 72. In FIG. 9C, there can be seen the inner module 74 movably mounted within the outer capsule 72. The movement of the inner module 74 can be accomplished by, for example, a gimbal arrangement, not shown, that can be a conventional mounting mechanism that permits the blood content detector 22 to move therein.

In FIG. 9D, there is shown a cross sectional diagram taken along the line 9D-9D of FIG. 9C illustrating the movement of the inner module 74 from its position at location X to its position at location Y. Accordingly, at position X, it can be seen that the measurement window 38 is located to the side and not facing the living tissue 40 where it must be to take a reading of the blood flow in that living tissue 40. The weights 68 thus operate to bring the inner module 74 to its position at location Y where the free movement of the inner module 74 within the outer capsule 72 repositions the measurement window 38 to the desired position contacting the living tissue 40 for a blood content reading. In this embodiment, the outer capsule 72 can have a substantially circular cross-section ellipsoidal shape as well as other possible shapes.

Figure 10:
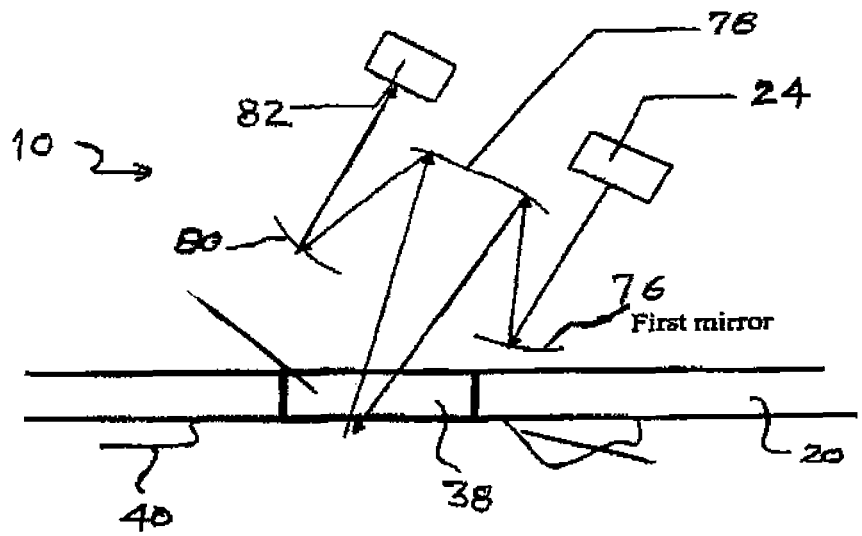
FIG. 10 is a schematic view of an alternate embodiment of the present invention using mirrors to guide the light traveling to and from the tissue of the patient.

Turning now to FIG. 10, there is shown a schematic view of the present invention where the lens (FIG. 2) has been replaced with a mirror arrangement in order to result in further miniaturization of the capsule 10. As such, with this embodiment, the light emitted by the light source 24 is reflected by two mirrors, a first mirror 76 and a second mirror 78 as that light passes through the window 38 to reach the living tissue 40. In a similar manner, the interacted light from the living tissue 40 is reflected off of two mirrors, the common, second mirror 78, and a third mirror 80 prior to reaching the photodetector 82. As can be seen the optical axis to the mirrors is inclined or at a non-90 degree angle with respect to the measurement window 38 so as to eliminate reflections from surfaces of the measurement window 38. In this embodiment, a spectroscope is suitable for the photodetector 82.

In the FIG. 10 embodiment, the illuminating light (polarized light) is emitted from the light source 24 so as to be parallel with the rotation symmetry axes of the first mirror 76 and the second mirror 78 (corresponding to the optical axes). Emitted light passes through a hole formed at the center of the first mirror 76 and reaches the surface of the living tissue 40. The light interacted with the living tissue 40 is reflected by the second mirror 78 and the third mirror 80 and reaches the spectroscope (photodetector 82). The surface of the living tissue 40 is positioned at the combined focus of the first and second mirrors 76, 78 so that the position of the spectroscope of the scattered light reaches varies depending on the scattering angle. Furthermore, the scattered light becomes in parallel with the optical axis near the spectroscope.

The mirrors should be arranged so that the image point (of the virtual image) of the first mirror 76 when the object point is the combined focus coincides with the "focal point of the second mirror 78". Where the first mirror 76 is a hyperboloid mirror and the second mirror 78 is a paraboloid mirror, optical aberrations may be reduced.

Figure 11:
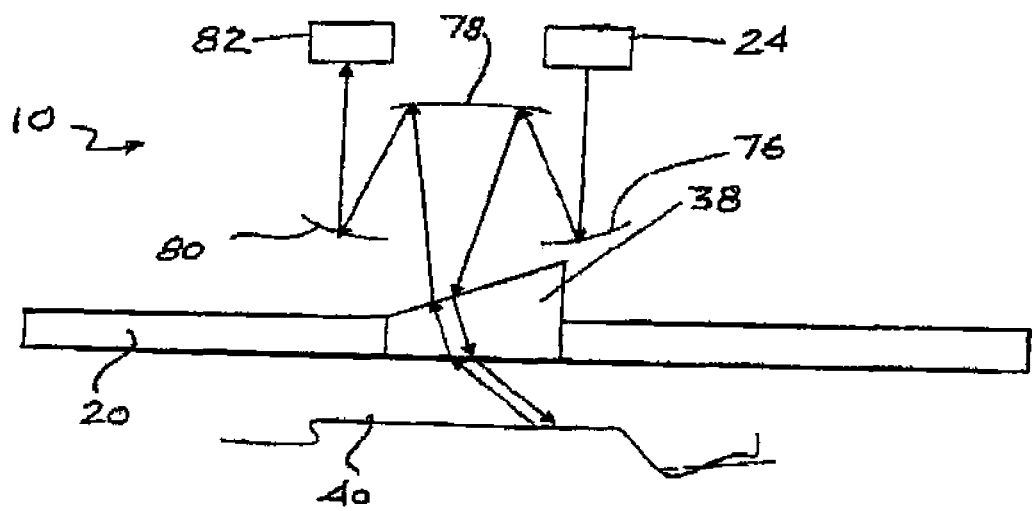
FIG. 11 is a schematic view of a further exemplary embodiment utilizing mirrors in the light path.

Turning now to FIG. 11, there is shown a schematic view similar to that of the FIG. 10 embodiment, however, the optical axes of the mirrors are perpendicular to the outer layer of the capsule 10 and the measurement window 38 is a wedge-shaped transparent member. This embodiment enables the reduction of stray light coming through the measurement window 38 and eliminates the need for inclining the optical axes of the mirrors as in the FIG. 8 embodiment, thereby simplifying the structure of the capsule 10.

Figure 12:
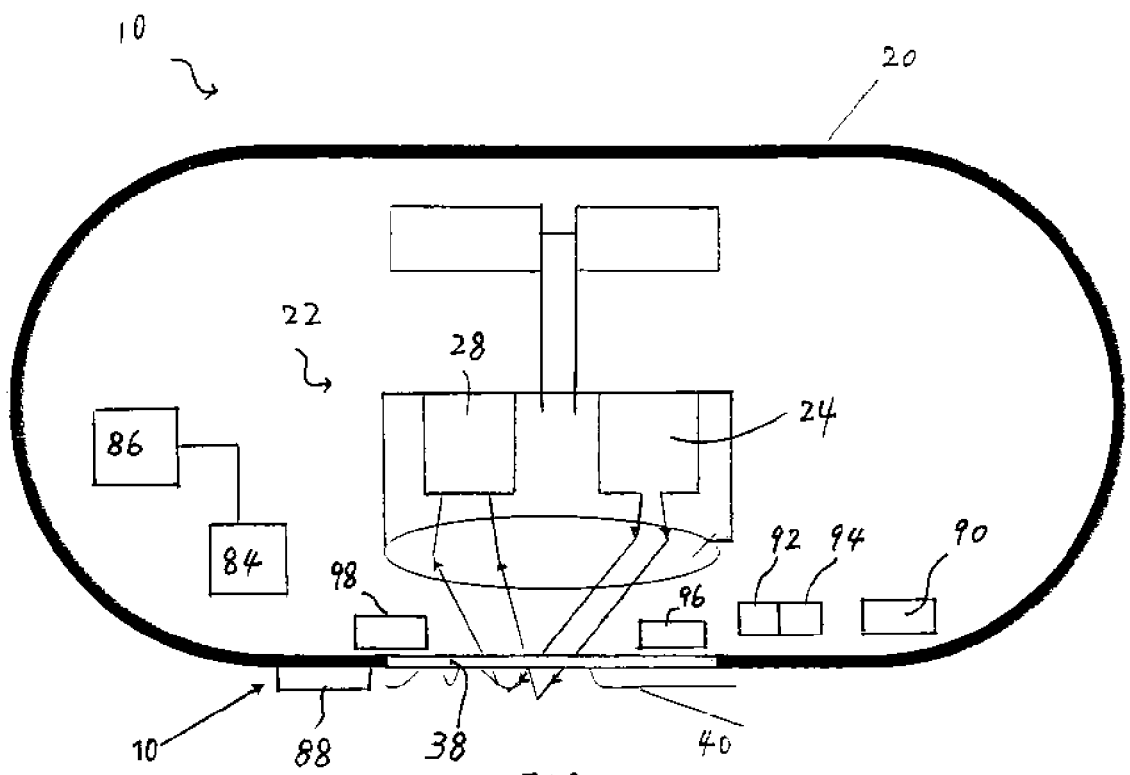
FIG. 12 is a cross sectional diagram of the present capsule having various proximity detecting systems.

Turning now to FIG. 12, there is shown a simplified cross sectional diagram of the capsule 10 of the present invention and, to explain this embodiment, FIG. 12 has been simplified with respect to FIG. 2 for example, it being understood that the FIG. 12 capsule 10 can have the similar components as described with respect FIG. 2. As such, the capsule 10 of FIG. 12 includes the capsule 20, the blood content detector 22, the illuminating means 16, the light receiving means 28 and the measurement window 38 that is shown to be contacting the living tissue 40.

As explained, with the capsule, it is important that the device be in actual contact with the living tissue 40 in order to obtain a valid reading of the blood content in that tissue. In this embodiment, there is a contact detector that alerts the user when there has been actual contact between the capsule 10 and the living tissue 40 of the patient. As an alternative, there can be a proximity detector that senses the approach of the capsule 10 to the living tissue 40 and which includes a contacting predicting means that sends a command to the overall system to commence a measurement of the blood content in the living tissue 40 when the actual contact is imminent. As used herein the term "proximity detector" will refer to a detector that senses the nearing and imminent proximity of the capsule to the living tissue as well as where the proximity is to the point where there is actual contact between the capsule and the living tissue.

Accordingly, in FIG. 12, in one exemplary embodiment, there is a proximity detector that comprises a image sensor 84 such as a camera, and which is directed toward the living tissue 32 along a path that is generally proximate to the path of the illuminating directed toward that living tissue 32 by the illuminating means 16. The image sensor 84 can receive the image of the living tissue 40 through the measurement window 38 or through an alternate window. The image sensor 84 includes an image analysis 86 that analyzes the image from the image sensor 84.

Basically, when an image sensor gets too close to a target so as to contact that target, the entire captured image takes on a substantially single color range. In the case of living tissue, that color range is typically a red color and the phenomenon is referred to as "redout". That image can, therefore, be analyzed in the image analysis 86 by comparing the signal value with the threshold for the average color of red. By such means, the system can detect the contact between the capsule 10 and the living tissue 40 of the patient. A signal can then be sent by the image analysis 86 wirelessly to enable the capsule 10 so that the light intensity of the illuminating means 24 can be intensified in order to obtain a reading of the blood content in that tissue, the actual contact having been verified.

As stated, when the redout condition is sensed, the light intensity of the illuminating means 24 is immediately increased so as to be a level sufficient for spectrometry and the measurement of the blood performed. After the measurement, the light intensity of the illuminating means 24 is rapidly returned to the pre-measurement value.

In another exemplary embodiment, the proximity detector may be a mechanical detector 88 located on the external contacting surface of the capsule 10 and the mechanical detector 88 can be sensitive to the mechanical contact between the capsule 10 and the living tissue 40. Further alternative embodiments of a proximity sensor include an electromagnetic signal sensor 90, a laser 92 and laser detector 94, a piezoelectric device 96, and an optical detector 98.

As an alternate embodiment of an intensity detector, there can be a system for detecting the distance between the capsule 10 and the living tissue 40 such that the distance determination means can predict how long the capsule 10 will take to come into actual contact with the living tissue and the system can signal the measurement system to start the onset of a measurement at the moment of contact.

Figure 13:
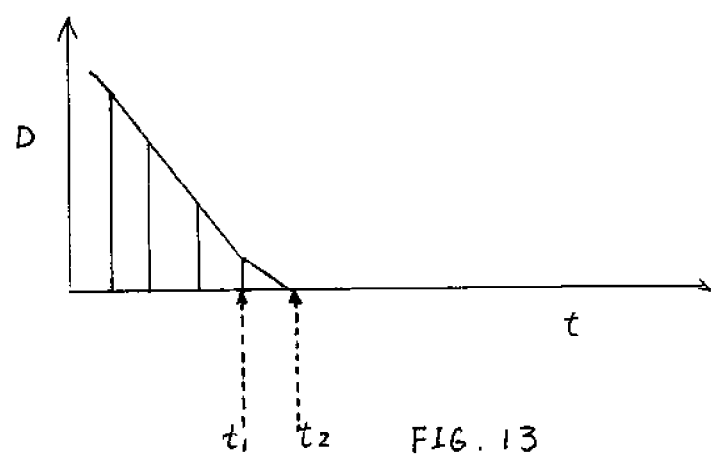
FIG. 13 is a graph plotting time vs. distance between a capsule and the living tissue of a patient.

Turning to the graph of FIG. 13, taken along with FIG. 12, signals transmitted from the distance sensor are continuously monitored for determining the distance between the capsule and the living tissue. The graph plots distance (D) between the capsule 10 and the living tissue 40 versus time (t). As can be seen, as the time progresses, the distance is narrowed to the time $t_1$ which is the point that a distance-detecting processor has determined that the actual contact is imminent. Thus, at $t_1$, the distance-detecting processor determines that the capsule will likely contact the living tissue before the next measurement of the distance according to the trend in the time axis, the processor commands the measurement system to start a measurement of the blood flow. Accordingly at time $t_2$, the actual measurement is taken.

The timeline of all system operations can be adjusted so that the time for that command to the actual start of a measurement is completely equivalent to the expected time until the contact of the capsule with the living tissue. Controlling the measurement system in such manner enables the accurate measurement even while a capsule is in contact with the living tissue.

In fact, the experienced time of contact does not always match the time of actual contact. The system may therefore have a means of monitoring the measurement results and evaluating the measurement results for their applicability in subsequent steps based on the fluctuation among different sets of measurement data or by comparing the final results with a predetermined threshold.

When considering the degree of invasion and acceptability by a patient, a capsule measurement type of device is highly desirable, however, it must be accurate at the time it is used. It is possible to correct a spectroscopic error due to a production error in the production process (which means storing correction data in the capsule). However, it is not possible to cope with an error of spectroscopic measurement value due to an optical element caused by vibration during transportation and changes of spectroscopic characteristics of illumination over time. Therefore, it is of great importance that the capsule be capable of easily being calibrated right before use.

Figure 14:
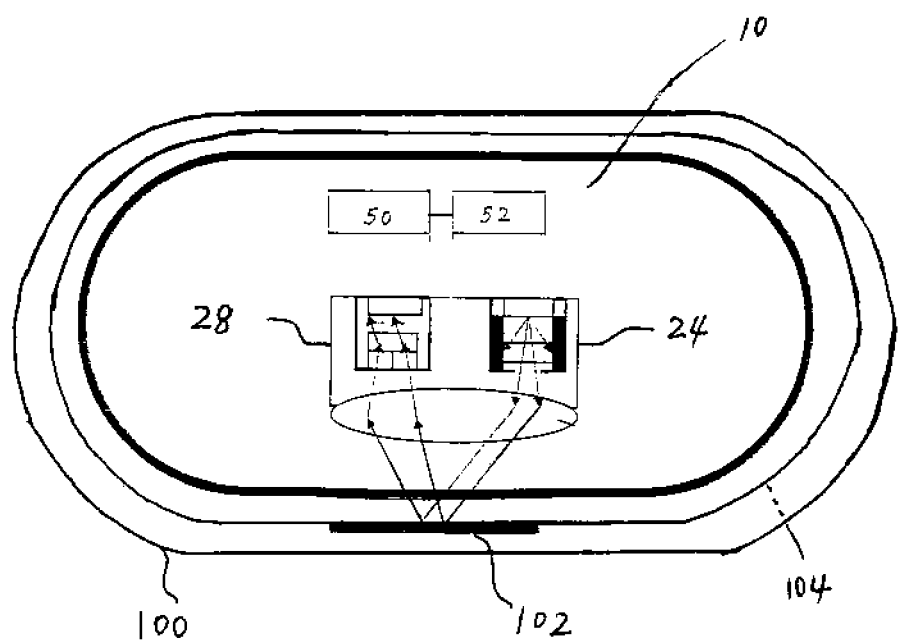
FIG. 14 is a cross sectional diagram illustrating a calibration system usable with the present invention.

Turning, therefore, to FIG. 14, there is shown a schematic view of a calibration system that meets those requirements. In particular, the capsule 10 is covered by a protective cap 100 so as to maintain the sterile conditions of the capsule 10. The protective cap 100 can be made of a transparent material that allows sterilizing gas to pass through but does not allow bacteria to penetrate. The protective cap 100 includes a white diffuser plate 102 that is disposed inside of the protective cap 100 so as to function as a calibration means. As can be seen, a beam of light emitted from the illuminating means 24 is diffused and reflected by the white diffuser plate 102 and directed to the light receiving means 28 and the Iw(λ) is measured and transmitted to the data processing means 58 (FIG. 1) where it is used in the equations carried out therein.

Accordingly in this embodiment because the capsule 10 maintains the sterile condition with the protective cap 100 affixed thereto, a user can conduct calibration before using the device and then remove the protective cap 100 from a notch 104, and can use the capsule 10 in a condition that is both sterilized and calibrated.

In addition, since a calibration means is provided inside the protective cap 100, calibration can be carried out near the outer surface of the capsule 10. Accordingly, because the quantity of the blood can be measured by making the outer surface of the capsule 10 come in contact with the living tissue of the patient, calibration can be carried out almost in the same state as an actual use thereof, thereby achieving highly accurate calibration. Furthermore, since a protective cap 100 and the white diffuser plate 102 are integrated into one unit, a user does not have to align the position of the calibration means with that of the capsule 10 so as to enable simple, easy operation.

Figure 15:
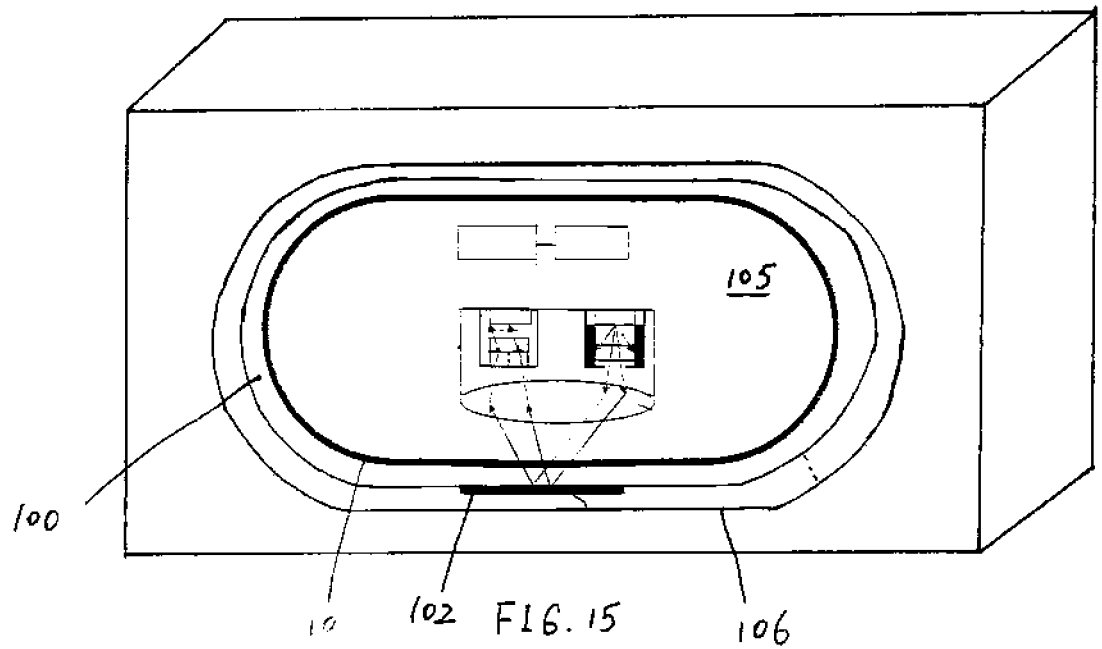
FIG. 15 is a cross sectional diagram illustrating an alternate calibration system usable with the present invention.

Turning, finally to FIG. 15, there is shown a further exemplary embodiment of the calibration system of the present invention. In this embodiment, there is a container 105 that contains the capsule 10 and a white diffuser plate 102 is disposed within the container 105. The container 105 is shown in the open position in FIG. 13. The container 105 has a recess 106 shaped like the outer shape of the capsule 10 and positioning can be accomplished by placing the capsule 10 within the recess 106.

At least a portion of the protective cap 100 reached by the light emitted from light source 24 is made of a material that is transparent with respect to the wavelength of the illuminating light. As with the FIG. 12 embodiment, calibration is carried out by use of the white diffuser plate 102.

In this embodiment, the user carries out calibration before using the capsule 10 and, by removing the protective cap 100 from the notch 104 (FIG. 14), and again the user has a capsule 10 that is both sterile and calibrated.

In addition, when compared to the FIG. 14 embodiment, because the white diffuser plate 102 is disposed inside the container 104, the material for that white diffuser plate 102 can be more widespread, thereby reducing the cost of the calibration system. A further advantage is that calibration can be carried out before the container 104 is opened which makes it possible that the effect of outside lights including room light, can be eliminated.

Those skilled in the art will readily recognize numerous adaptations and modifications which can be made to the of the present invention which will result in an improved device and method of using the same, yet all of which will fall within the scope and spirit of the present invention as defined in the following claims. Accordingly, the invention is to be limited only by the following claims and their equivalents.

What is claimed is:

1. A device comprising;
   a capsule configured for swallowing and movement within the digestive tract, said capsule having a transmitter and a blood content detector for detecting blood content within mucosal tissue forming a body lumen of the digestive tract, wherein the blood content detector comprises:
   a light source configured to emit light outwardly relative to said capsule for interacting with the mucosal tissue;
   an optical detector that detects interacted light from the mucosal tissue that is originated from said light source;

a light source linear polarizer configured to polarize the light emitted by the light source; and a first and a second linear polarizers placed between the mucosal tissue and the optical detector and configured to polarize the interacted light from the mucosal tissue, a polarizing direction of the first linear polarizer being same as that of the light source linear polarizer and a polarizing direction of the second linear polarizer being perpendicular to that of the first linear polarizer; and wherein said transmitter is coupled to said optical detector for receiving signals from said optical detector indicative of the detected interacted light from the mucosal tissue and for transmitting signals to an external processor; said transmitted signals being indicative of blood content within said mucosal tissue.

2. The device of claim 1 further comprising an image capture device disposed in said capsule.

3. The device of claim 1 further comprising a measurement window formed within the capsule and wherein the optical detector is disposed adjacent said window.

4. The device of claim 3 wherein said capsule is configured to locate said window in contact with said mucosal tissue when employed in vivo.

5. The device of claim 4 wherein said configuration includes a shape for facilitating said window positioning in vivo.

6. The device of claim 4 wherein said configuration includes a center of gravity to utilize gravity for facilitating said window positioning in vivo.

7. The device of claim 6 further comprising at least one weight to achieve said center of gravity.

8. The device of claim 1 wherein the blood content detector is selectively moveable within said capsule.

9. The device of claim 8 further comprising a module moveably disposed within said capsule, wherein said blood content detector is mounted to said module.

10. The device of claim 9 wherein the capsule has at least a part of a circular cross-section shape.

11. The device of claim 9 wherein the capsule has at least a part of an ellipsoidal cross-section shape.

12. The device of claim 9 further comprising a gimbal, wherein said blood content detector is mounted to said gimbal.

13. The device of claim 9 further comprising at least one measurement window disposed within said capsule, wherein said blood content detector is an optical detector.

14. The device of claim 13 wherein the blood content detector comprises a light source and an optical detector.

15. The device of claim 14 wherein the blood content detector further comprises at least one reflector.

16. A device of claim 15 wherein said at least one reflector is positioned within said capsule to reflect light produced by said light source through the measurement window onto the surface of a living tissue.

* * * * *